United States Patent [19]

Rickett

[11] 4,119,100

[45] Oct. 10, 1978

[54] SURGICAL DEVICE FOR DISCHARGE OF FAECAL MATTER FROM THE COLON

[76] Inventor: John William Stanley Rickett, 33 Bronescombe Ave., Bishopsteignton, Teignmouth, Devon TQ14 9SR, England

[21] Appl. No.: 778,950

[22] Filed: Mar. 18, 1977

[51] Int. Cl.² .................. A61M 27/00; A61F 5/44
[52] U.S. Cl. ............................ 128/350 R; 128/283; 128/349 B; 138/93
[58] Field of Search ............... 128/283, 325, 246, 344, 128/348–351; 138/93

[56] References Cited

U.S. PATENT DOCUMENTS

| 2,820,457 | 1/1958 | Phillips | 128/351 |
| 3,693,624 | 9/1972 | Shiley et al. | 128/351 |
| 3,802,418 | 4/1974 | Clayton | 128/283 |
| 3,828,782 | 8/1974 | Polin | 128/283 |

Primary Examiner—Dalton L. Truluck
Attorney, Agent, or Firm—Birch, Stewart, Kolasch & Birch

[57] ABSTRACT

A surgical device for discharge of faecal matter from the colon comprises a bent drainage duct whose inner end lies within the lumen of the colon and is surrounded by an inflatable bag for filling the lumen, the outer end of the duct projecting through the side of the inflatable bag and through the wall of the colon. The outer end of the duct is held in position by a flange which lies against the surface of the patient's skin and is coupled to the duct.

6 Claims, 2 Drawing Figures

SURGICAL DEVICE FOR DISCHARGE OF FAECAL MATTER FROM THE COLON

BACKGROUND OF THE INVENTION

Field of the Invention

The present invention relates to a surgical device for the discharge of faecal matter from the colon.

When a segment of the colon is removed because of localized disease, there is risk that healing of the subsequent anastomosis will be hindered by faecal matter present in the lumen. For this reason it has been the practice to prepare the bowel prior to the operation and to temporarily defunction the part of the colon in the region of the anastomosis after resection. To this end a colostomy is effected for the discharge of the faeces through the abdominal wall into a colostomy bag. A second operation is normally necessary to close the colostomy after healing of the anastomosis.

SUMMARY OF THE INVENTION

In accordance with the present invention there is provided a surgical device for discharge of faecal matter from the colon when a part of the colon is to be temporarily defunctioned, the device comprising a bent drainage duct so dimensioned that its inner end can lie within the lumen of the colon while its outer end extends through the wall of the colon, a flange disposed around the outer end of the drainage duct to lie against the outer surface of the abdominal wall, and an inflatable bag surrounding the drainage duct and designed, when inflated, to fill the lumen of the colon, the inner end of the drainage duct projecting from one end of the inflated bag while the outer end projects from the side wall of the bag.

In the use of this device, the drainage duct with the deflated bag is inserted in the colon through a small incision in the wall of the colon which is provided with a purse-string suture. The bag is then inflated to occlude the lumen of the colon.

A point proximal to the anastomosis is chosen for the insertion of the device. Two encircling ligatures are placed around the colon on either side of the point where the outer end of the drainage duct passes through the wall of the colon. These ligatures snug the colon on to the inflated bag to prevent the passage of faecal matter. A skin incision is made in the anterior abdominal wall to allow the outer end of the drainage duct to be passed through. In one embodiment the outer end of the drainage duct is a separate extension tube which can be coupled to a drainage tube forming the inner part of the duct by a screw connection on other convenient coupling and which carries the flange. In this case the extension tube is inserted from outside at a point overlying the drainage tube and is then coupled to the latter. In a second embodiment the drainage duct is in one piece and is passed through the incision from the inside, the flange being thereafter placed over the outer end of the drainage duct and secured in position against the skin. For this purpose the flange is integral with a threaded boss over which a threaded ring can be screwed and an O-ring is disposed between the boss and the ring to grip the outer surface of the drainage duct when compressed between the ring and the boss.

In each case a colostomy bag is attached to the outer end of the drainage duct.

The device is easily removed by deflation of the bag and withdrawal of the drainage tube. The abdominal wall will then heal without the necessity of any second operation to close it such as was previously required with a colostomy.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in more detail with the aid of examples illustrated in the drawing which are given by way of illustration only, and thus are not limitative of the present invention, and wherein.

DETAILED DESCRIPTION OF THE INVENTION

Figure 1:
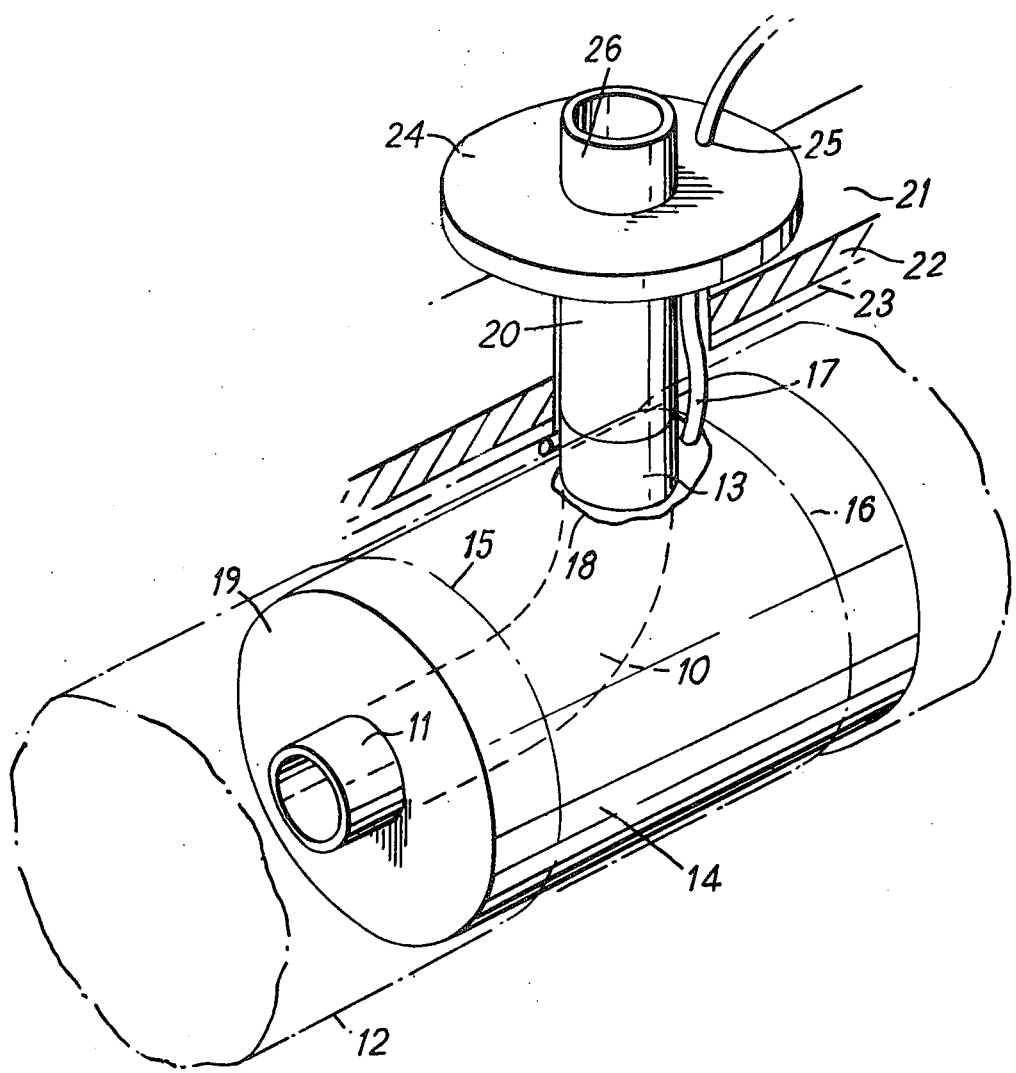
FIG. 1 illustrates a perspective view of the device in accordance with the present invention as shown positioned in the colon of a patient.

Referring first to FIG. 1, the device shown comprises a drainage tube 10 whose inner end 11 lies along the axis of the colon 12. The tube 10 is bent so that its outer end 13 extends perpendicular to the inner end 11 and passes radially through the wall of the colon 12. Surrounding and attached to the tube 10 is a soft rubber bag which is inflatable to the cylindrical shape shown so that it will fill the lumen of the colon and act as an obturator. Encircling ligatures 15 and 16 tie the colon to the cylindrical wall of the bag 14. An inflation tube 17 for the bag enters the bag close to the point at which the outer end 13 of the drainage tube passes through the cylindrical wall of the bag. A purse-string suture 18 surrounds the opening in the wall of the colon through which the tube 10 and inflation tube 17 passes. The inner end 11 of the drainage tube 10 projects centrally from the end wall 19 of the bag 14.

The outer end 13 of the drainage tube 10 is provided with an external screw thread (not shown) on to which the inner end of an extension tube 20 is screwed. The tube 20 passes through the subcutaneous tissue 21, the muscle layer 22, and the peritoneum 23. Near the outer end of the tube 20 is a flange 24 to rest against the skin. The inflation tube 17 passes through an aperture 25 in the flange 24. The outer end of the tube 20, beyond the flange 24 is expanded to receive a colostomy bag.

In a typical example, the drainage tube 10 and the extension tube 20 have an internal diameter of $\frac{3}{4}$ inch. The bag when inflated has a length of 4 inch and a diameter of $2\frac{1}{2}$ inch. The inner end 11 of the drainage tube projects $\frac{1}{4}$ inch from the bag while the outer end 13 projects $\frac{1}{2}$ inch up to the bottom of the screw thread. The flange 24 of the extension tube is 2 inch in diameter and is fixed $\frac{1}{2}$ inch from the outer end of the tube. The length of the extension tube below the flange may be varied to suit requirements. Both tubes are rigid. The tube 10 passes through the side wall of the inflatable bag at least $1\frac{1}{4}$ inch from the end of the bag.

Figure 2:
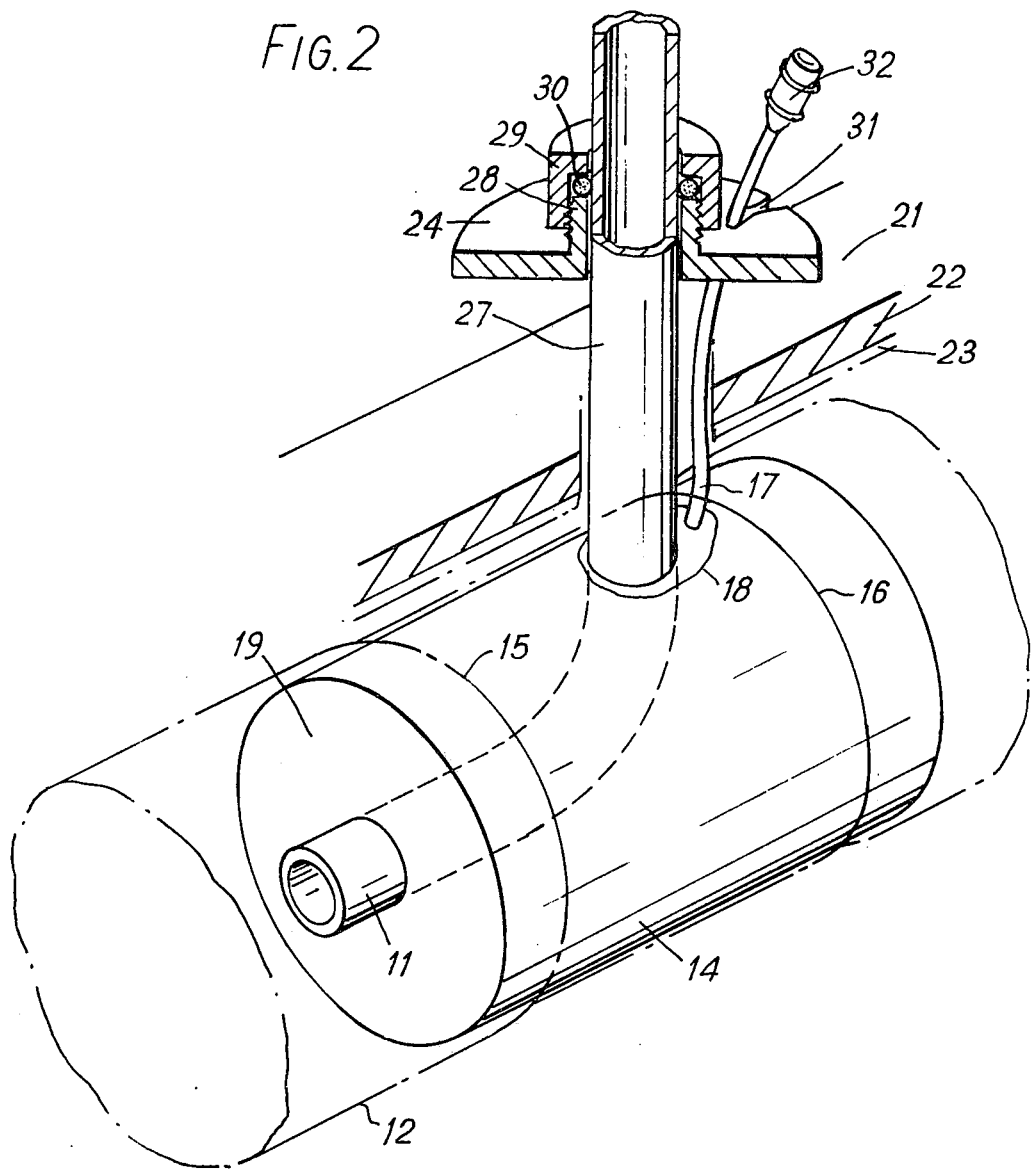
FIG. 2 illustrates a view similar to FIG. 1 of a second embodiment of the device of the present invention which shows in partial cutaway the interior construction thereof.

It will be seen that in the embodiment of FIG. 1 the extension tube 20 when joined to the main drainage tube 10 forms a continuous drainage duct. In the embodiment of FIG. 2, on the other hand, the drainage duct is formed as a single tube 27. Parts in FIG. 2 which correspond to those of FIG. 1 have been given the same reference numerals and will not be described again.

The outer end of the drainage tube 27 carries the flange 24 which is integral with a threaded boss 28 which is slidable along the tube 27. A threaded ring 29 engages with the boss 28 and an O-ring 30 is held captive between the ring 29 and the boss 28. When the ring 29 is screwed down, the O-ring 30 is deformed to engage the outer surface of the tube 27 and thus hold the flange 24 in position. The flange 24 is provided with a key-hole slot 31 to receive the inflation tube 17. The outer end of the tube 17 is fitted with a valve 32.

It will be appreciated that the device of FIG. 2 is used in a similar manner to that of FIG. 1, with the difference that the drainage tube 27 is passed through the skin incision from the inside after the tube and the bag 14 have been inserted in the colon. The flange 24 is then fitted on the outer end of the drainage tube and secured in position against the outer surface of the skin. The inflation tube 17 is passed through at the same time and fitted in the slot 31 in the flange 24.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A surgical device for discharge of faecal matter from the colon when a part of the colon is to be temporarily defunctioned, the device comprising:
    a bent drainage duct so dimensioned that its inner end can lie within the lumen of the colon while its outer end extends through the wall of the colon;
    a flange disposed around the outer end of the drainage duct to lie against the outer surface of the abdominal wall; and
    an inflatable bag surrounding the drainage duct, the inflated bag having a generally cylindrical form to fill the lumen of the colon, the inner end of said drainage duct projecting from one end of the inflated bag and the outer end projecting from a side wall of the bag.

2. A surgical device as claimed in claim 1 in which the drainage duct comprises a drainage tube surrounded by the inflatable bag and an extension tube capable of being coupled to the drainage tube after insertion through the abdominal wall, the flange being carried by the extension tube.

3. A surgical device as claimed in claim 2 having a screw connection between the drainage tube and the extension tube.

4. A surgical device as claimed in claim 1 in which the drainage duct is a single continuous tube and the flange is removably carried by the outer end of the drainage tube.

5. A surgical device as claimed in claim 4 in which the flange is attached to a threaded boss slidable on the drainage tube and a threaded ring engaged with the boss traps an O-ring which is deformable by screwing down the threaded ring to secure the flange in position on the drainage tube.

6. A surgical device for discharge of faecal matter from the colon when a part of the colon is to be temporarily defunctioned, the device comprising:
    a drainage duct so dimensioned that a bent portion can lie within the lumen of the colon while its outer end extends through the wall of the colon;
    an inflatable bag surrounding said bent portion of said drainage duct positioned within the lumen of the colon;
    said inflatable bag being generally cylindrical in shape so that when inflated it conforms to the shape of the lumen of the colon;
    said bent portion of said drainage duct projecting from one end of said generally cylindrical inflatable bag;
    said outer end of said drainage duct projecting from a side wall of said generally cylindrical inflatable bag and extending through the wall of the colon; and
    a flange disposed around said outer end of said drainage duct to lie against the outer surface of the abdominal wall.

* * * * *